United States Patent [19]

Boris-Lawrie

[11] Patent Number: 5,770,428
[45] Date of Patent: Jun. 23, 1998

[54] CHIMERIC RETROVIAL EXPRESSION VECTORS AND PARTICLES CONTAINING A SIMPLE RETROVIRAL LONG TERMINAL REPEAT, BLV OR HIV CODING REGIONS AND CIS-ACTING REGULATORY SEQUENCES, AND AN RNA TRANSLATIONAL ENHANCER WITH INTERNAL RIBSOME ENTRY SITE

[75] Inventor: Kathleen A. Boris-Lawrie, Columbus, Ohio

[73] Assignee: Wisconsin Alumni Research Foundation, Madison, Wis.

[21] Appl. No.: 627,845

[22] Filed: Apr. 3, 1996

Related U.S. Application Data

[63] Continuation-in-part of Ser. No. 264,115, Jun. 22, 1994, Pat. No. 5,554,524, which is a continuation of Ser. No. 21,622, Feb. 17, 1993, abandoned.

[51] Int. Cl.⁶ .............................. C12N 7/00; C12N 7/01; C12N 15/00; C12N 15/09
[52] U.S. Cl. .................. 435/235.1; 435/236; 435/172.3; 435/320.1; 424/199.1; 424/207.1; 424/208.1
[58] Field of Search .................................. 435/69.1, 69.3, 435/70.1, 172.3, 235.1, 236, 320.1; 424/187.1, 188.1, 199.1, 207.1, 208.1

[56] References Cited

U.S. PATENT DOCUMENTS

| 4,937,190 | 6/1990 | Palmenberg et al. .................. | 435/69.1 |
| 5,554,524 | 9/1996 | Termin et al. ........................ | 435/235.1 |

FOREIGN PATENT DOCUMENTS

| 611822 | 8/1994 | European Pat. Off. . |

OTHER PUBLICATIONS

H.M. Termin, *A proposal for a new approach to a preventive vaccine against human immunodeficiency virus type 1*, 90 Proc. Natl. Acad. Sci. USA 4419–4420 (1993).

K. Boris–Lawrie, et al., *Genetically Simpler Bovine Leukemia Virus Derivatives Can Replicate Independently of Tax and Rex*, 69 J. Virol. 1920–1924 (1995).

I.R. Ghattas, et al., *The Encephalomyocarditis Virus Internal Ribosome Entry Site Allows Efficient Coexpression of Two Genes from a Recombinant Provirus in Cultured Cells and in Embryos*, 11 Mole. Cell. Biol. 5848–2849 (1991).

K.A. Boris–Lawrie, et al., *Recent advances in retrovirus vector technology*, 3 Curr. Opin. Genet. and Develop. 102–109 (1993).

M.A. Adam, et al., *Internal initiation of translation in retroviral vectors carrying picornavirus 5 untranslated regions*, 65 J. Virol. 4985–4990 (1990).

H–M. Koo, et al., *Spleen necrosis virus, an avian retrovirus, can inflect primate cells*, 65 J. Virol. 4769–4776 (1991).

(List continued on next page.)

*Primary Examiner*—Ponnathapura Achutamurthy
*Assistant Examiner*—Jeffrey S. Parkin
*Attorney, Agent, or Firm*—Quarles & Brady

[57] ABSTRACT

This invention is directed toward novel replication competent retroviral expression vectors and particles containing a single chimeric viral genome composed of a simple retroviral (e.g., spleen necrosis virus [SNV]) long terminal repeat (LTR), complex retroviral (e.g., Bovine Leukemia Virus [BLV] or Human Immunodeficiency Virus [HIV]) gag, pol, and env coding regions, complex retroviral cis-acting sequences (e.g., the encapsidation signal [E], primer binding site [PBS], polypurine tract [PPT], and att sites), and an RNA translational enhancer containing an internal ribosome entry site (IRES). These chimeric viral genomes express the BLV or HIV gag, pol, and env genes in a tax/rex- or tat-/rev-independent manner, respectively. Moreover, the inclusion of an IRES site in the modified viral genome facilitates the expression of the env gene products. These retroviral vectors and particles provide a source of viral antigens that can be employed in both diagnostic assays and as immunogens for the production of specific immunological reagents.

8 Claims, 2 Drawing Sheets

OTHER PUBLICATIONS

R.A. Morgan, et al., *Retroviral vectors containing putative internal ribosome entry sites: development of a polycistronic gene tranfer system and applications to gene therapy*, 20 Nucleic Acids Res. 1293–1299 (1992).

J. Ban, et al., *Use of monoclonal antibodies in an ELISA for the diagnosis of bovine leukaemia virus infection*, 30 J. Virol. Meth. 79–88 (1990).

D. Portelle, et al., *Use of two monoclonal antibodies in an ELISA test for the detection of antibodies to bovine leukaemia virus envelope protein gp51*, 23 J. Virol. Meth. 211–222 (1989).

M. Bray, et al., *A Small element from the Mason–Pfizer monkey virus makes human immunodeficiency virus type 1 expression and replication Rev–independent*, 91 Proc. Natl. Acad. Sci. USA 1256–1260 (1994).

Brenner, M., 1994, Immunomethods 5:204–210.

Lieden, J., 1995, New Engl. J. Med. 333(13):871–873.

Mulligan, R., 1993, Science 260:926–932.

Graham et al., 1995, New Engl. J. Med. 333:1331–1339.

Haynes, B., 1993, Science 260;1279–1286.

CHIMERIC RETROVIAL EXPRESSION VECTORS AND PARTICLES CONTAINING A SIMPLE RETROVIRAL LONG TERMINAL REPEAT, BLV OR HIV CODING REGIONS AND CIS-ACTING REGULATORY SEQUENCES, AND AN RNA TRANSLATIONAL ENHANCER WITH INTERNAL RIBSOME ENTRY SITE

This is a continuation-in-part of U.S. Ser. No. 08/264,115, filed Jun. 22, 1994, now U.S. Pat. No. 5,554,524, which in turn is a file wrapper continuation of U.S. Ser. No. 08/021,622 filed Feb. 17, 1993, now abandoned.

This invention was made with United States government support awarded by the National Institute Of Health (NIH), Grant No. CA07175 and CA22443. The United States government has certain rights in this invention.

FIELD OF THE INVENTION

The present invention relates to recombinant retroviruses that are useful to produce diagnostic antigens and vaccines.

BACKGROUND OF THE INVENTION

Retroviruses are a type of RNA virus that replicates through a DNA intermediate. As described in European patent application 611,822 A2; K. Boris-Lawrie, et al., 69 J. Virol. 1920–1924 (1995); and H. Temin, 90 P.N.A.S. U.S.A. 4419–4420 (1993) there are simpler "S Type" and more complex "MC Type" retroviruses. The disclosure of these publications, and of all other publications referred to herein, are incorporated by reference as if fully set forth herein.)

All retroviruses have gag, pol, and env genes. For some retroviruses (e.g. spleen necrosis virus; murine leukemia virus) only these genes are needed for viral replication. Such viruses are called "simpler" or "S Type" retroviruses. (See e.g. U.S. Pat. Nos. 4,650,764; 4,980,289; and 5,124,263). Other retroviruses, called "more complex" or "MC Type" retroviruses, need additional genes for replication. Among the more complex retroviruses are human immunodeficiency virus (HIV) and bovine leukemia virus (BLV).

The genomes of both simpler and more complex retroviruses have some common features. Both types of RNA viruses replicate through a DNA intermediate. Therefore, both simpler and more complex retroviruses have DNA and RNA genomes. The viral DNA genomes for both types of retroviruses are bounded by long terminal repeats (LTRs). These LTRs contain enhancer, promoter, usually 3' RNA processing sequences, and integration sequences ("att").

In nature, simpler retroviruses are found in various non-mammalian hosts (e.g. birds), or lower mammalian hosts, but not primates or ungulates. In contrast, more complex retroviruses are prevalent in ungulates and primates, including humans.

The additional genes of the more complex retroviruses are associated with pathogenesis in their hosts and are essential for replication of the natural virus. In this regard, the additional genes in more complex retroviruses are known to code for proteins that act on transcription, splicing, and polyadenylation.

As described in EP 611,822 A2, our laboratory designed viruses (and vectors for producing them) where Gag and Pol protein from a MC Type virus were produced from one vector having simpler type LTR, and where Env protein from a MC Type virus was produced from a second vector having simpler type LTR. This "complementary vector" system was efficient in propagating an S Type derivative of the natural MC Type virus, creating antigens for diagnostic assays.

While the complementary vector approach has shown some utility for vaccination purposes, the duration of immunity provided by it for any given dose is expected to be lower than optimal because virus spread is somewhat limited due to the complementary vector configuration. Multiple treatments and/or high doses may therefore be needed to achieve sustained immunity.

As taught in U.S. Pat. No. 4,937,190, there is a class of RNA translational enhancers (coded for by DNA) that have a RNA base sequence that also appears in a cardiovirus RNA enhancer base sequence located 3' of a cardiovirus polyC sequence of over 50 base pairs and 5' of a cardiovirus AUG initiation sequence. One such enhancer is coded for by such a region in encephalomyocarditis virus. Other such enhancers are present in other cardioviruses (e.g. picornaviruses). These enhancers allow for translation initiation from an internal ribosome entry site. Thus, I refer to cardioviral RNA translational enhancers herein by the designation "IRES".

There have been proposals to use IRES enhancers to provide improved expression of a non-retroviral gene that is positioned on a retroviral vector (e.g. an antibiotic resistance gene) along with normal retroviral proteins in those circumstances in which the non-retroviral gene might not otherwise be efficiently expressed. See e.g. K. Boris-Lawrie, et al., 3 Curr. Op. Gen. Dev. 102–109 (1993); M. Adams, et al., 65 J. Virol. 4895–4990 (1991); H-M. Koo, et al., 65 J. Virol. 4769–4776 (1991); R. Morgan, et al., 20 Nuc. Acids Res. 1293–1299 (1992); I. Ghattas, et al., 11 Mol. Cell. Biol. 5848–5859 (1991); and K. Boris-Lawrie, et al., 69 J. Virol. 1920–1924 (1995).

In connection with creating "mixed" MC Type retroviral vaccines (that have simpler type LTR) we removed the tax and rex of bovine leukemia virus and the tat and rev of HIV. However, when Env is not expressed from a separate vector from Gag and Pol (i.e. when Gag, Pol and Env are all on the same vector), and when rex/rev tax/tat are deleted, this interferes with efficient expression of Env. Insertion of an internal (DNA) transcriptional promoter downstream of gag and pol to drive transcription of env does not adequately solve this problem. Among other things the expression from the internal promoter is unstable over time.

Thus, a need exists for a mixed MC Type virus (and vectors for producing them) where the virus induces a strong protective response in a mammalian host.

SUMMARY OF THE INVENTION

The invention provides a recombinant retroviral vector capable of expressing a replication competent retroviral virus particle. There is a S Type retroviral long terminal repeat and also DNA encoding MC Type retroviral protein. The expression vector encodes MC Type att, pbs, E, and ppt, but not at least one of MC Type tax or rex. Preferably, the expression vector does not encode S Type att. The encoded MC Type retroviral protein is bovine leukemia viral Env, Gag, and Pol protein. There is also DNA coding for an IRES translational enhancer, the DNA being positioned on the vector 5' to an env coding sequence and 3' to at least one of the gag and pol coding sequences.

In another aspect, the invention provides a replication competent retroviral virus particle. There is a RNA sequence having S Type retroviral long termini and encoding a MC Type att, pbs, E and ppt, but not at least one of MC Type tax or rex. The encoded MC Type retroviral protein is bovine leukemia viral Env, Gag, and Pol protein, and there is an IRES translational enhancer positioned on the RNA sequence 5' to an env coding sequence and 3' to at least one of the gag and pol coding sequences.

In another aspect relating to HIV, the invention provides a recombinant retroviral vector capable of expressing a replication competent retroviral virus particle. Again, there is a S Type retroviral long terminal repeat and DNA encoding MC Type retroviral protein. In this case, the expression vector encodes MC Type att, pbs, E, and ppt, but not at least one of MC Type tat or rev. Further, the encoded MC Type retroviral protein is human immunodeficiency viral Env, Gag, and Pol protein, and there is DNA coding for an IRES translational enhancer positioned on the vector 5' to an env coding sequence and 3' to at least one of the gag and pol coding sequences.

Figure 1A:
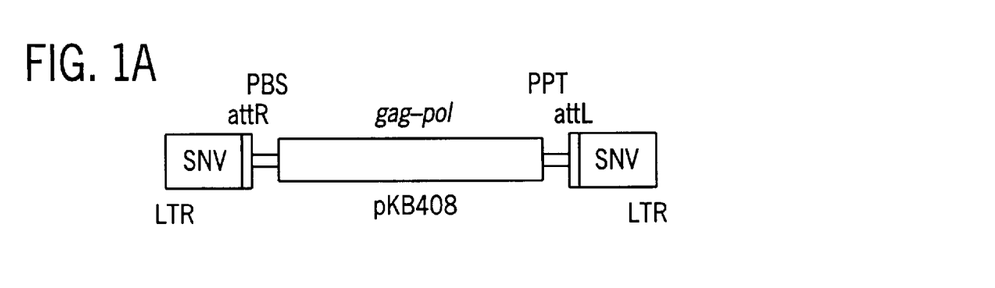
Figure 1B:
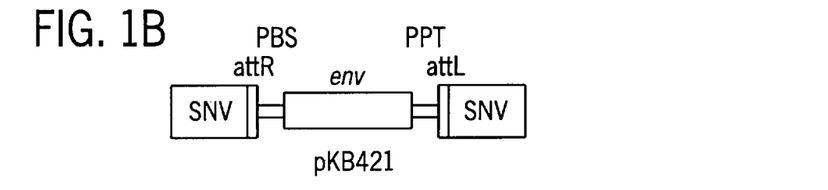
Figure 1C:
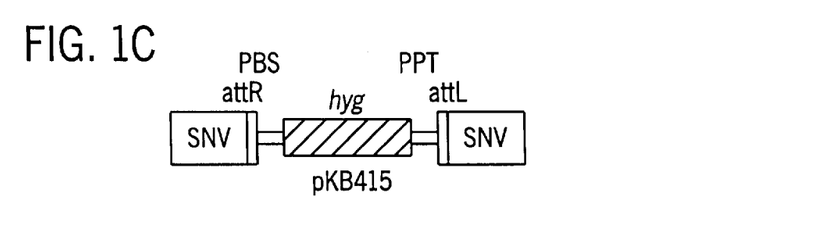
Figure 2:
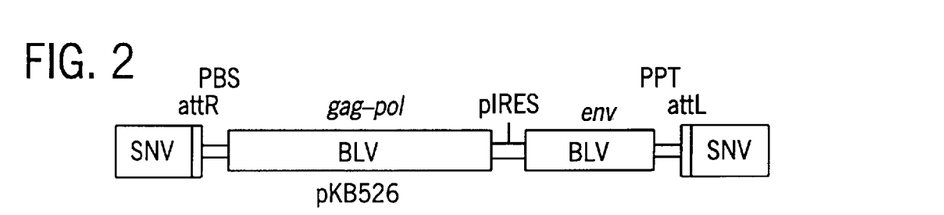

In yet another HIV version, there is a replication competent retroviral virus particle. It has a RNA sequence having S Type retroviral long termini and encodes MC Type att, pbs, E and ppt, but not at least one of tat or rev. The encoded MC Type retroviral protein is human immunodeficiency viral Env, Gag, and Pol protein, and there is an IRES translational enhancer positioned on the RNA sequence 5' to an env coding sequence and 3' to at least one of the gag and pol coding sequences.

Methods of using such vectors and viruses are also disclosed. One can use the virus to produce a retroviral protein in a live mammalian host. The protein acts as an antigen in the host and raises an immune/protective response (e.g. utility as a vaccine). Preferred host are mammals within the host range of BLV such as murine, bovine, and sheep, and mammals within the host range of HIV such as murine, primate, or human.

It has been surprisingly discovered that even with the specified removals of rev and rex which have splicing function, the use of the IRES upstream of env permits efficient expression of Gag, Pol and Env from a single vector, resulting in a virus that raises an antigenic response in a host. In the single vector configuration, virus spread should be more efficient than on the complementary vector configuration.

To achieve greater efficiency in connection with HIV, a constitutive transport element ("CTE") from Mason-Pfizer (a S-Type retrovirus) monkey virus was inserted 3' of the env. The element acts constitutively to transport unspliced RNA from the nucleus to the cytoplasm. See M. Bray, 91 P.N.A.S. USA 1256–1260 (1994).

Another strategy to achieve HIV efficiency inserts a HIV rev gene 3' of env, and a IRES is positioned 5' of rev to facilitate efficient translation of Rev protein. In this case, tat is missing.

An object of the present invention is to efficiently produce diagnostic antigens which include certain, but not all, MC Type retroviral proteins.

Another object of the present invention is to produce a replication competent virus that has S Type retroviral long terminal repeats except for att, encodes MC Type retroviral proteins, and which is suitable for use as a vaccine when injected into a host.

It is another object of the present invention to provide a virus of the above type wherein the virus will be likely to mutate similarly to the way the naturally occurring MC Type retrovirus would when in a host.

Another object of the invention is to provide vectors for producing such viruses.

Other features, objects and advantages of the present invention will become apparent after a review of the following specification, and claims, and the drawings (e.g. methods for using the virus). Thus, the claims should be looked to in order to assess the full scope of the invention.

DESCRIPTION OF THE DRAWINGS

FIG. 1 is a schematic diagram of three prior art vectors capable of collectively expressing a BLV derivative that can replicate and providing a selection marker;

FIG. 2 is a schematic diagram of a BLV vector of the present invention;

FIG. 3 is a schematic diagram of a HIV vector of the present invention; and

FIG. 4 is a schematic diagram of a second HIV vector of the present invention.

DESCRIPTION OF THE PREFERRED EMBODIMENTS

Vectors pKB408, pKB421 and pKB415 (FIG. 1) were starting materials in connection with the present invention. Their construction has been described in our laboratory's EP 611,822 A2, and in its U.S. counterpart (U.S. Ser. No. 08/264,115). In connection with these applications they were deposited in host D17 dog cells with the American Type Culture Collection, Rockville, Md., U.S.A. Accession No. ATCC 11259 on Feb. 2, 1993 under the terms of the Budapest Treaty. Samples from the deposits will be made available in accordance with U.S. and applicable foreign patent law requirements. Deposit of these materials does not imply that a license for their use has been granted.

I chose these as starting materials as they contain on pKB408 gag and pol of bovine leukemia virus (BLV), and on pKB421 BLV env, and on pKB415 an antibiotic marker.

In the wild type, BLV has tax and rex genes, in addition to gag, pol, and env genes. The products of the tax and rex genes act on sequences in the BLV long terminal repeats (LTRs). Our laboratory has previously constructed chimeric retrovirus DNA vectors from BLV and the simpler retrovirus spleen necrosis virus (SNV). We substituted simpler retrovirus cis-acting control sequences from SNV for most of the more complex retrovirus control sequences found in BLV and deleted some sequences coding for regulatory genes (tax/rex). We replaced all of the BLV LTRs except for the terminal attachment sequences (attR and attL), about 10 base pairs on each end, with the analogous sequences from the LTR of SNV and deleted the BLV tax and rex genes. However, the experimental gag-pol and env genes were (in EP 611,822 A2) expressed on separate chimeric vectors.

In accordance with the present invention, a poliovirus IRES was amplified by PCR from pP2–5' (residues 117–747), a plasmid that contains the 777 base pair poliovirus 5' untranslated sequence. The IRES was subcloned into pCRII (Invitrogen) to generate pKB451. Alternatively, an IRES is available at ATCC 67525 as described in U.S. Pat. No. 4,937,190. The PCR primers (SEQ ID NO.:1 and SEQ ID NO.:2) introduce SalI and SmaI restriction sites at each end of the IRES sequence.

The BLV env gene was PCR amplified from pKB421 using primers that introduce terminal MscI and SalI sites (SEQ ID NO.:3 and SEQ ID NO.:4). The PCR product was subcloned into pCRII (Invitrogen) to create pKB450. pKB450 was digested with MscI to release the BLV env gene, which was subcloned into pKB451 at compatible SmaI sites to generate pKB453.

pKB453 was digested with SphI (which flank the IRES env fragment) and the IRES env fragment was subcloned into pKB426 at the unique SphI site to generate pKB526, the single hybrid BLV genome (FIG. 2). One can create pKB426 from pKB408. One amplifies sequences from BLV U5 to −1 gag in BLV by PCR with primers SEQ ID NOS.:13 and 14 which add terminal EcoRI and KpnI restriction sites, respectively. After digestion of pKB408, the PCR product with EcoRI and KpnI ends was inserted to yield pKB426.

HIV Vectors

HIV retroviral sequences may similarly be used in the present invention to create retroviral vectors containing simpler retroviral LTRs flanking HIV retroviral sequences. The DNA sequences (and functions of those sequences) for a wide variety of complex retroviruses are known. See e.g. G. Myers, *Human Retroviruses And AIDS* (Theoretical Biology And Biophysics) (1990) (HIV-1).

For example, one could attach simpler retrovirus SNV LTR sequences to internal HIV att, Pbs, E, Ppt and coding sequences. It is necessary that sufficient HIV sequences be present to produce a replication competent system, but at least one HIV sequence should be deleted (e.g. tat of HIV, HIV NL4-3 sequences numbers 5830–6044, and the LTRs deleted sequence numbers 61–611 and 9121–9737) by the above techniques and then inserted in place of the BLV sequence. If desired, still other HIV-1 sequences could be removed (e.g. rev, vif, vpr, upu, nef).

A S Type HIV has in fact been constructed by taking the HIV-1 gag, pol, and env genes (a source of these genes being the cell line HUT78 (HIV-1$_{SF2}$) found in the N.I.H. AIDS Research And Reference Reagent Program Catalog #279, January 1992, National Institutes Of Health, Publication No. 2-1536, and replacing the cis-acting LTR control sequences acted on by the Tat protein of HIV-1 with the transcription and polyadenylation sequences from SNV. In particular, as for BLV, this construct was created by substituting simpler retrovirus LTR sequences for all of the HIV-1 LTR sequences except for the att sequences. Such a substitution also deleted HIV tat and rev sequences. If desired, more HIV-1 proteins can be left in (e.g. vpu, vif) to facilitate replication, albeit at least one HIV-1 protein should be deleted (preferably tat). The result was the vector of FIG. 4.

Alternatively, I inserted a constitutive transport element "CTE" at the XbaI and SalI restriction site in HIV env as follows. HIV$^{LAV}$ sequences 100 to 2040 were PCR amplified with primers that add terminal EcoRI and XbaI sites (SEQ ID NOS.:5 and 6), and subcloned into pKB504 to generate pKB504 gag. To create pKB504, pKB408 could be digested with EcoRI and HindIII and in place of the BLV sequences, a PCR product containing HIV-1 3' untranslated sequences inserted to make pKB504. The PCR primers contain EcoRI and HindIII termini and HIV-1 pNL4-3 sequences 9059–9095 are SEQ ID NOS.:15 and 16.

Sequences 1521 to 4655 were amplified with primers that add terminal XbaI sites and the PCR product was subcloned into PCRII and designated pCRIIpol. This plasmid was digested with ApaI (1557) and XbaI (4655), and the ApaI/XbaI pol fragment was inserted into pKB504gag that had been digested with ApaI and XbaI to generate pKB504gagpol.

The HIV env gene was PCR amplified with primers that add terminal MscI and XbaI sites (SEQ ID NOS.:7 and 8), and subcloned into pCRII to create pKB612. After digestion with MscI, the HIV env gene was ligated 3' of polio IRES in PKB451 to generate pKB474. (The IRES env fragment was then subcloned downstream of gagpol in pKB504gagpol at the site to create pKB504gagpolenv-not shown).

Figure 3:
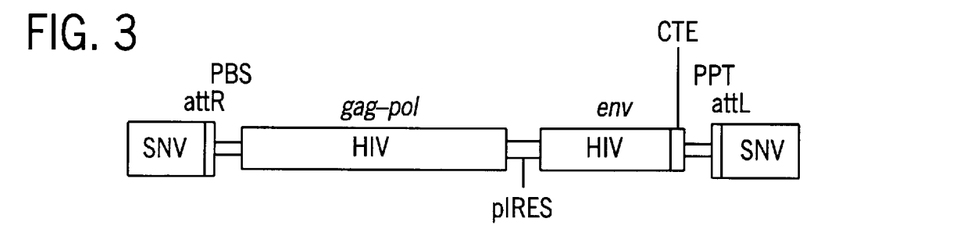

The CTE was amplified by PCR from Mason-Pfizer monkey virus proviral DNA with primers that add terminal XhoI and SalI sites (SEQ ID NOS.:9 and 10), and subcloned into pCRII to generate pKB471. The CTE was then subcloned on an XhoI/SalI fragment into PKB474 to generate pKB475. pKB475 was digested with XbaI and SalI and the IRESenvCTE fragment was ligated at homologous sites in pKB504gagpol to create pKB504gagpolenvCTE as shown in FIG. 3.

Figure 4:
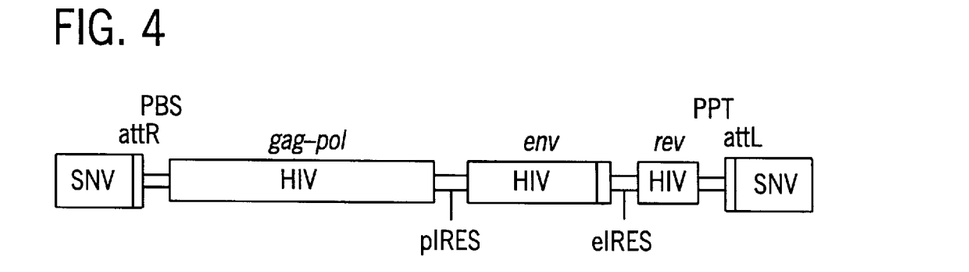

HIV rev was amplified using PCR primers with MscI and SphI sites (SEQ ID NOS.:11 and 12) and inserted into pCRII to make pCRIIrev. The EMCV IRES was cloned 5' of rev using MscI/SphI sites and designated pKB470. Then the IRESrev fragment from pKB470 (XhoI/SalI) was inserted into the XhoI site of pKB474 to create pKB476. Finally, pKB476 was digested with XbaI and SalI and the IRESenvIRESrev fragment was ligated into the homologous restriction sites in pKB504gagpol to create pKB504gagpolenvrev as shown in FIG. 4.

If a different env is desired, the amphotropic MLV env gene can be subcloned from pJD1 (Doughtery, et al., J. Virol., 63: 3209–3212 (1989)) on an XbaI fragment and ligated at the XbaI site of a vector as described in EP 611,822.

Diagnostic Tests

One utility for such vectors (and for viruses produced therefrom) is to generate an array of retroviral proteins from them that can be used as antigens in an ELISA or other immunoassay. For example, the ELISA protocol described below uses such a recombinant antigen to detect antibodies in serum from infected animals. S Type BLV virus can be generated from the vector plasmids in D17 dog osteosarcoma cells, and used to infect fresh D17 target cells. The cells, which now produce replicated S Type BLV variants, can then be lysed using standard freezing and sonication techniques, and the lysate containing viral antigens can be harvested after centrifugation of cell debris.

Microtiter plates can be coated with either D17/recombinant BLV lysate preparation, or a negative control uninfected D17 lysate preparation, or a positive control BLV-infected Bat clone 6 cell-free virus preparation, at several dilutions in 0.1M $Na_2CO_3$ and incubated overnight at 4° C. The plates can then be washed three times in standard ELISA washing buffer (0.15M NaCl with 0.05% Tween 20). Serum from a known BLV-infected sheep (or unknown) can be diluted in a standard ELISA diluent (0.15M NaCl, 1 mM EDTA, 0.05 Tris (pH 7.4), 0.05% Tween 20, 0.1% BSA and 2% nonfat dry milk), and 0.1 ml can be added to each well and incubated for 2 hours at 37° C.

The plates can be washed three times with ELISA washing buffer and anti-sheep (or anti-bovine) IgG-horse radish peroxidase conjugate can be added and incubated for 1 hour at 37° C. The plates can be washed three times and a developing substrate (preferably ABTS [2,2'-azino-di-(3-ethyl-benzthiazoline sulphate)] (0.11 mg/ml) in 0.05M citric acid and 0.008% $H_2O_2$), can be added and incubated with shaking for 30 minutes. The reaction can be stopped by adding 0.1 ml 10% SDS and the OD405 determined spectrophotometrically in a standard ELISA plate reader. See generally De Portetelle, 23 J. Virol. Meth. 211–223 (1989).

An HIV diagnostic test can be performed in a similar manner, with the substitution of the mixed recombinant HIV antigen for the mixed recombinant BLV antigen, and the substitution of an anti-human IgG.

Replication Competency

To test the in vitro replication capacity of the single genome simple BLV derivative, the following protocol was performed: D17 cells were co-transfected with the single genome simple BLV provirus DNA and a selectable vector (e.g. pHyg). Three days later virus-containing cell-free medium was harvested and was used to infect fresh D17 target cells. The infected cells were selected for hygromycin resistance and subsequently progeny virus was harvested from the infected cells (passage 1 cells) and used to infect fresh target cells (passage 2 cells). The resulting virus was analyzed, and I confirmed the presence of the desired gag, pol and env.

Murine Experiments

A passage 1 clone designated D17/5B6 was used for inoculation of rats. The cells for rat inoculation were grown in Dulbecco's modified medium containing 5% of fetal calf serum and Hygromycin B (80 units/ml). Adult male Wistar rats 200–300 g in weight were used. Blood was collected from the tail vein of the experimental rats at various periods of time. The blood from the rats was tested for levels of the expected antibody using Western blot analysis. Antibody to the BLV, Gag and Env antigens were confirmed.

Sheep Tests

Six sheep were injected intradermally with three doses of 400 ug DNA in liposomes (DOTAP) in three week intervals as follows:

| | |
|---|---|
| 1–2 | 2 sheep-single genome S Type BLV provirus (pKB526) in DOTAP from Boehringer Mannheim Biochemical (BMB); |
| 3–4 | 2 sheep-single genome S Type BLV provirus (pKB526) in DOTAP from Waisman Center Vector Core Laboratory; |
| 5 | 1 sheep-wild-type BLV provirus pBL913 in DOTAP from BMB.; and |
| 6 | 1 sheep-control. |

After 4 months, the sheep were challenged with blood from a BLV seropositive sheep. Sheep 1–4 showed no adverse effects to date from the vaccine or challenge. Monitoring is still continuing to assess long term benefits.

Primate Experiments

Efficiency of antibody response in a primate (e.g. for HIV-1) may be tested in a chimpanzee and SIV-macaque model system. See R. Desrosiers, AIDS Res. Hu. Retrovir., 8: 411–21 (1992) and M. D. Daniel, et al., Science 258: 1938–41 (1992). If desired, a killed vaccine (which can be made from the virus) could be used.

In the alternative, the live construct could be partially crippled by mutating promoter and enhancer sequences or adding a suicide gene expressed from a picornaviral internal ribosome entry site. F. L. Moolten, et al., J. Natl. Canc. Inst., 82: 297–305 (1990); C. A. Mullen, et al., Proc. Natl. Acad. Sci. USA, 89: 33–7 (1992); and I. R. Ghattas, et al., Mol. Cell. Biol., 11: 5848–59 (1991).

To prepare a live chimeric virus for use in raising an antibody response (e.g. for use as a potential vaccine), supernatant medium from infected cells could be harvested, filtered (0.4 um pore size) to remove cells, and concentrated by ultracentrifugation at 35,000 RPM for 2 hours. The virus preparation would preferably be administered intravenously (Marthas, et al., J. Virol. 64: 3694 (1990)). It is expected that concentrations of chimeric virus in the range of 0.5 to 5.0 ml will be injected under a subcutaneous or intramuscular protocol until an antibody response is raised in a mammal. Alternative, proviral DNA could be directly injected subcutaneously.

To determine an effective amount of the recombinant retrovirus or retroviral protein for use in a vaccine, one would typically create preparations with increasing amounts of retrovirus proteins. One would then develop a protocol to determine when a sufficient amount of preparation had been administered to a test animal to raise an antibody response and/or provide disease resistance.

The following is a preferred method to develop an inactivated viral vaccine virus is harvested from the supernatant medium of cells infected with chimeric virus. The supernatant medium is centrifuged, preferably at 10,000 RPM, to remove cells and concentrated by ultracentrifugation, preferably at 35,000 RPM for 2 hrs. To inactivate the chimeric virus, the virions are resuspended in formalin (0.8%) and incubated at 4° C. for 24 hr. See Salk, et al., Ann. NY Acad. Sci. 83: 609 (1960); Marx, et al. J. Virol. 60: 431 (1986); and Montefiori, et al., J. Virol. 64: 5223 (1990).

To ensure that the chimeric virus is inactivated, an aliquot of the formalin-treated virus could be washed free of formalin and used to infect D17 target cells. The recovery of chimeric virus could be monitored by reverse transcriptase assay or by a vector rescue assay. See Miller, Hum. Gene Therapy 1: 5 (1990). To assist the immunogenic effect of the formalin treated-vaccine, the vaccine could be combined with an adjuvant, such as threonyl muramyl dipeptide. See Allison and Byars, J. Immuno. Methods 95: 157 (1986). The preparation is preferably administered intramuscularly (Montefiori, et al., supra, J. Virol. 64: 5223 (1990)).

It is expected that when sufficient virus or viral protein is used the immune response will be such that the host will be immunized. Thus, the viruses, crippled or killed sources thereof, or the proteins they express, could act as vaccines for BLV or HIV (and other more complex retrovirus). In this regard, humans, other primates, and ungulates all have an antibody and a protective immune responses to S Type retroviruses.

Because the viruses are missing more complex retroviral proteins critical to the disease, no retroviral disease like those caused by the original more complex retrovirus should result from exposure to the recombinant retroviruses.

Industrial Applicability

In any event, regardless of the utility as a vaccine or immunity inducer, as noted above there is significant value in being able to obtain a supply of more complex retroviral Env, Gag, and/or Pol protein that is produced in large quantity by a replication competent retroviral vector in the absence of other more complex retroviral proteins. This is especially so when the vector has gone through multiple infection cycles (and thus genetic variants have been generated). For example, the present invention is useful in raising focused antigens that can be used via the Kohler/Milstein (or other techniques) to raise monoclonal antibodies.

The invention is thus not to be limited to the above preferred embodiments. Rather, attention should be directed to the claims to judge the full scope of the invention.

I claim:

1. A recombinant retroviral expression vector containing a single replication competent hybrid retroviral genome comprising the following elements:
   i) a simple retrovirus (S-type) long terminal repeat (LTR);
   ii) the bovine leukemia virus (BLV) gag, pol, and env genes;
   iii) the bovine leukemia virus (BLV) encapsidation signal (E), primer binding site (PBS), polypurine tract (PPT), and att site; and,
   iv) a nucleic acid encoding for an RNA translational enhancer containing an internal ribosome entry site (IRES) and positioned on the vector 3' to the gag and pol genes and 5' to the env gene;
wherein said expression vector is capable of producing retroviral particles in at least one of a tax- or rex-independent manner.

2. The recombinant retroviral expression vector of claim 1 wherein said vector does not contain an S-type att site and is incapable of encoding for the tax or rex gene products.

3. A replication competent retrovirus particle containing a single hybrid retroviral genome comprising the following elements:
   i) a simple retrovirus (S-type) long terminal repeat (LTR);
   ii) the bovine leukemia virus (BLV) gag, pol, and env genes;
   iii) the bovine leukemia virus (BLV) encapsidation signal (E), primer binding site (PBS), polypurine tract (PPT), and att site; and,
   iv) a nucleic acid encoding for an RNA translational enhancer containing an internal ribosome entry site (IRES) and positioned on the vector 3' to the gag and pol genes and 5' to the env gene;
wherein said retroviral genome is capable of being expressed in at least one of a tax- or rex-independent manner.

4. The replication competent retrovirus particle of claim 3 wherein said single hybrid retroviral genome does not contain an S-type att site and is incapable of encoding for the tax or rex gene products.

5. A recombinant retroviral expression vector containing a single replication competent hybrid retroviral genome comprising the following elements:
   i) a simple retrovirus (S-type) long terminal repeat (LTR);
   ii) the human immunodeficiency virus (HIV) gag, pol, and env genes;
   iii) the human immunodeficiency virus (HIV) encapsidation signal (E), primer binding site (PBS), polypurine tract (PPT), and att site; and,
   iv) a nucleic acid encoding for an RNA translational enhancer containing an internal ribosome entry site (IRES) and positioned on the vector 3' to the gag and pol genes and 5' to the env gene;
wherein said expression vector is capable of producing retroviral particles in at least one of a tat- or rev-independent manner.

6. The recombinant retroviral expression vector of claim 5 wherein said vector does not contain an S-type att site and is incapable of encoding for the tat or rev gene products.

7. The recombinant retroviral expression vector of claim 5 wherein said vector comprises the following additional elements:
   v) a rev gene positioned on the vector 3' to the gag, pol, and env genes; and,
   vi) a nucleic acid encoding for an RNA translational enhancer containing an internal ribosome entry site (IRES) and positioned on the vector 3' to the gag, pol, and env genes and 5' to the rev gene.

8. A replication competent retrovirus particle containing a single hybrid retroviral genome comprising the following elements:
   i) a simple retrovirus (S-type) long terminal repeat (LTR);
   ii) the human immunodeficiency virus (HIV) gag, pol, and env genes;
   iii) the human immunodeficiency virus (HIV) encapsidation signal (E), primer binding site. (PBS), polypurine tract (PPT), and att site; and,
   iv) a nucleic acid encoding for an RNA translational enhancer containing an internal ribosome entry site (IRES) and positioned on the vector 3' to the gag and pol genes and 5' to the env gene;
wherein said retroviral genome is capable of being expressed in at least one of a tat- or rev-independent manner.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:1:

GTCGACCAGC TCTGGGGTTG TTCCC     25

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:2:

CCCGGGCATT GAGTGGTGAT GATATCAAC     29

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:3:

TGGCCAAAAG AACGACGGTC CCG     23

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:4:

GTCGACTCAA GGGCAGGGTC G     21

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:5:

GAATTCAAGT AGTGTGTGCC CGTCTGTTG 29

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: Other nucleic acid     (xi) SEQUENCE DESCRIPTION: SEQ ID NO:6:

TCTAGATGTC CACAGATTTC TATGAGTATC 30

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: Other nucleic acid     (xi) SEQUENCE DESCRIPTION: SEQ ID NO:7:

AATGGCCAAG AGTGAAGGAG AAGTATC 27

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear     (ii) MOLECULE TYPE: Other nucleic acid     (xi) SEQUENCE DESCRIPTION: SEQ ID NO:8:

AAGTCGACTT ATAGCAAAAT CCTTTCCAAG C 31

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: Other nucleic acid     (xi) SEQUENCE DESCRIPTION: SEQ ID NO:9:

CTCGAGAGAC TGGACAGCCA ATGACG 26

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear     (ii) MOLECULE TYPE: Other nucleic acid     (xi) SEQUENCE DESCRIPTION: SEQ ID NO:10:

GTCGACAATT ATAAAAACA AAAGACAC 28

(2) INFORMATION FOR SEQ ID NO:11:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: Other nucleic acid ( x i ) SEQUENCE DESCRIPTION: SEQ ID NO:11:

AATGGCCATC GGAAGAAGCG GAGACAGCG      29

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:12:

AGCATGCGTC GACACTATTC TTTAGTTCCT GACTCC      36

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:13:

GAATTCCCCG CGTTTGTTTC CTGTCTTAC      29

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:14:

GGTACCATAT AATTTGAAGG AGAGACCC      28

( 2 ) INFORMATION FOR SEQ ID NO:15:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:15:

GAATTCAAAA GAAAAGGGGG GACTGGAAGG GCTAATTCAC TCCA      44

( 2 ) INFORMATION FOR SEQ ID NO:16:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear (ii) MOLECULE TYPE: Other nucleic acid (xi) SEQUENCE DESCRIPTION: SEQ ID NO:16:

AGCTTGGAGT GAATTAGCCC TTCCAGTCCC CCCTTTTCTT TTGAATTC                48